United States Patent [19]

McKean

[11] 4,340,038
[45] Jul. 20, 1982

[54] MAGNETIC FIELD CONCENTRATION MEANS AND METHOD FOR AN IMPLANTED DEVICE

[75] Inventor: Brian D. McKean, Sepulveda, Calif.

[73] Assignee: Pacesetter Systems, Inc., Sylmar, Calif.

[21] Appl. No.: 216,540

[22] Filed: Dec. 15, 1980

[51] Int. Cl.³ .............................................. A61B 5/02
[52] U.S. Cl. .................................... 128/1.3; 128/748; 219/10.43; 219/10.79; 219/10.57
[58] Field of Search ............................... 128/1.3, 748; 219/10.43, 10.79, 10.57

[56] References Cited
U.S. PATENT DOCUMENTS

| | | | |
|---|---|---|---|
| 2,765,389 | 10/1956 | Van Iperen | 219/10.79 |
| 3,462,336 | 8/1969 | Leatherman | 219/10.43 |
| 3,846,609 | 11/1974 | Enk | 219/10.79 |
| 3,958,558 | 5/1976 | Dunphy et al. | 128/748 |
| 4,014,319 | 3/1977 | Favre | 128/748 |
| 4,062,354 | 12/1977 | Taylor et al. | 128/748 |

*Primary Examiner*—Kyle L. Howell
*Assistant Examiner*—Nancy A. B. Swisher
*Attorney, Agent, or Firm*—John F. Buskirk

[57] ABSTRACT

A magnetic field concentration means and method for use in conjunction with an implanted device responsive to an externally generated magnetic field. More specifically, a magnetic field concentrator is disclosed which includes a metallic slug located between a magnetic field generator and a magnetic pick-up coil contained in the implanted device. The metallic slug concentrates magnetic lines of flux at the pick-up coil. In a specific embodiment, the implanted device is an intracranial pressure monitoring device (ICPM) which is located within an orifice formed in a recipient's skull. The magnetic field concentrator is positioned within the orifice and directly above the ICPM, thereby concentrating magnetic flux lines at the ICPM. Two configurations of the slug are disclosed, one being in the form of a cylinder and the other being in the form of a truncated cone. In another application of the concentrator, a bandage or other suitable holding means positions the slug externally to the implanted device, thereby again concentrating magnetic lines of flux at the implanted device.

12 Claims, 8 Drawing Figures

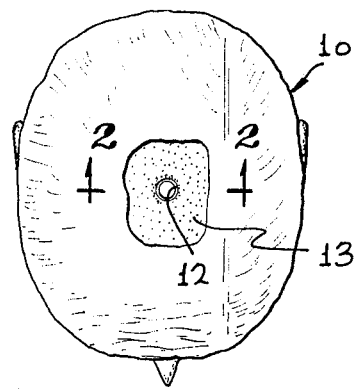
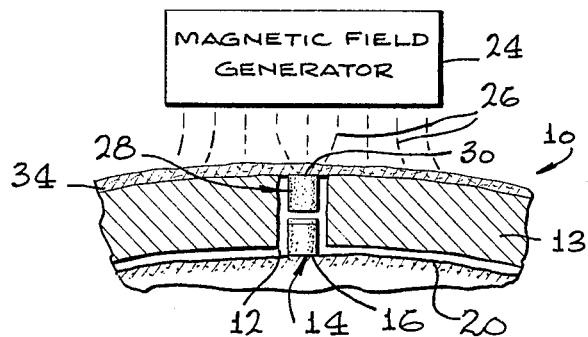
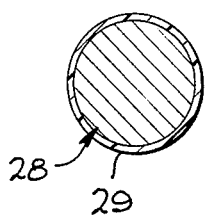
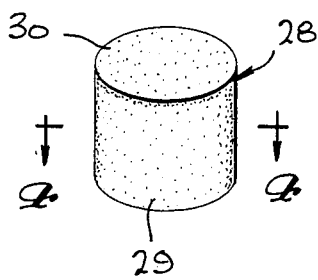
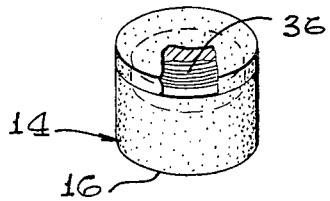
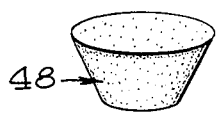
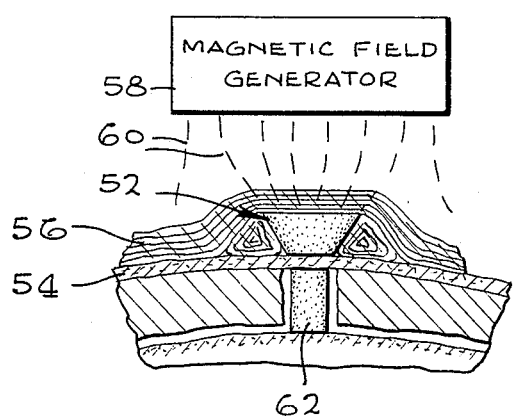

MAGNETIC FIELD CONCENTRATION MEANS AND METHOD FOR AN IMPLANTED DEVICE

FIELD OF THE INVENTION

The invention relates to devices implantable in humans, and more specifically to apparatus and methods for transferring power from an external device to an implanted device.

BACKGROUND OF THE INVENTION

Many types of implantable devices incorporate a self-contained transducer for converting magnetic energy from an externally-located magnetic field generator to energy usable by the implanted device. In such a system having an implanted device and an externally-located magnetic field generator for powering the device, sizing and design of the power transfer system is important. In order to properly design the power transfer system while at the same time avoiding overdesign, the distance from the implanted device to the magnetic field generator must be known. However for some types of implanted devices the depth of the implanted device in a recipient's body is variable, and is not known until the time of implantation by a surgeon. One example of such a device is an intracranial pressure monitoring device (ICPM) wherein skull thickness varies considerably between recipients and the device must be located so that it protrudes slightly below the inner surface of the skull and contacts the dura, thereby resulting in a variable distance between the top of the implanted device containing a pick-up coil or transducer and the outer surface of the skull. One conventional technique for accommodating an unknown distance between the magnetic field generator and the implanted device includes increasing the transmission power of the external magnetic field generator. However this increased power can result in heating of the implanted device, the excess heat being potentially hazardous to the recipient. A further technique has been to increase the diameter of the pick-up coil in the implanted device. However, physical size constraints imposed on many implanted devices such as the ICPM are critical; and increasing the diameter of the pick-up coil is undesirable in that it increases the size of the orifice which must be formed in the recipient's skull. The concentrator of the present invention solves the above problems by concentrating magnetic lines of flux from the magnetic generator at the implanted pick-up coil, the concentrator being adapted to accommodate distance variations between the implanted device and the magnetic field generator.

SUMMARY OF THE INVENTION

In a system including an implanted device having a magnetic field pick-up means and an external magnetic field generator located so that magnetic lines of flux generated thereby intersect the pick-up means, the invention provides a means for concentrating a portion of the magnetic lines of flux at the pick-up means which includes a metallic slug located between the generator and the pick-up means, thereby concentrating the magnetic lines of flux at the pick-up means. In addition, the invention provides a method for increasing the magnetic flux density at an implanted device having a magnetic pickup means, the method including the steps of locating a magnetic field generator a predetermined distance from the pick-up means, and placing a metallic slug between the generator and the pick-up means, thereby increasing the flux density at the pick-up means.

More specifically, the slug can either be implanted or externally located with respect to the implanted device, and formed in a plurality of shapes. Specific shapes disclosed include a cylindrical shape and a truncated cone shape. In the exemplary embodiment, the implanted device is an intracranial pressure monitoring device (ICPM) which is located in an orifice formed in the skull of the recipient by a surgeon. Skull thicknesses vary from recipient to recipient, and the ICPM must be located within the orifice so that a pressure sensing surface thereof extends below the inner surface of the skull and slightly depresses the dura. In one configuration, the slug is coated with a body-inert material and located within the orifice and positioned directly above the implanted device. Its size is chosen at the time of implantation so that its upper surface is substantially flush with the outer surface of the skull. Thus magnetic lines of force from the magnetic field generator are gathered and concentrated by the slug and provided to the magnetic pick-up coil contained within the implanted ICPM. This scheme is unique in that it solves the power transfer problem for those cases where power transfer distance is to be minimized, yet it does not necessitate a bulky implanted device, a high power magnetic field generation capability, or a plurality of implanted devices designed for different recipients. In addition, the metallic slug is a physically separate entity from the active implanted device, inexpensive, safe and easy to use.

BRIEF DESCRIPTION OF THE DRAWINGS

FIG. 1 is a top view of a recipient's skull showing the metallic slug positioned therein;

FIG. 2 is a cross-sectional view of the recipient's skull taken along line 2—2 of FIG. 1;

FIG. 3 is a perspective view of the slug shown in FIG. 2;

FIG. 4 is a cross-sectional view taken along line 3—3 of FIG. 3;

FIG. 5 is a cut-away, perspective view of an intracranial pressure monitoring device (ICPM) showing location of a magnetic pick-up coil contained therein;

FIG. 6 is a cross-sectional view of the recipient's skull showing a metallic slug in the form of a truncated cone;

FIG. 7 is a perspective view of the slug shown in FIG. 5; and

FIG. 8 is a cross-sectional view showing a slug externally positioned with respect to the recipient's skin.

DETAILED DESCRIPTION

Detailed illustrative embodiments of the invention disclosed herein exemplify the invention and are currently considered to be the best embodiments for such purposes. However, it will be apparent to those skilled in the art that changes and modifications may be made without departing from the invention in its broader aspects. Accordingly, the specific embodiments disclosed are only representative in providing a basis for the claims which define the scope of the present invention.

As previously explained, many types of conventional implantable devices are adapted to operate in response to energy provided by an externally located magnetic field generator. Typically, magnetic flux density at the implanted device must be above a predetermined level in order for the device to operate properly. As is well known, flux density at the implanted device is related to the power of the magnetic field generator and its distance from the device. Typically, the implanted device and magnetic field generator are designed so that this distance is relatively small. If the distance between a magnetic pick-up coil in the implanted device and the magnetic field generator is greater than anticipated, then the magnetic field generator may not be able to provide the flux density required at the implanted device for proper operation. Disclosed is a magnetic field concentrator in the form of variously-shaped metallic slugs which can be located between the magnetic field generator and the implanted device. The slug is configured so that magnetic lines of flux from the magnetic field generator intersect with and are captured by the slug. The slug directs the captured magnetic flux lines to the implanted device, the flux density being greater at the implanted device than it would have been without use of the slug.

In FIG. 1, a top view of a recipient's head 10 is shown. In this exemplary embodiment, an intracranial pressure monitoring device (ICPM) is utilized as the implanted device. The purpose of the ICPM is to provide a means for measuring pressure being exerted on the recipient's dura, and providing access to this measured pressure by an external receiving means. Typically, implantation of the ICPM is effected by forming a hole or orifice 12 in the recipient's skull 13, the orifice 12 being chosen so that the ICPM can be placed therein.

Referring to FIG. 2, an ICPM 14 is shown located in the orifice 12 so that its lower or pressure-sensitive surface 16 abuts against the recipient's dura 20. A magnetic field generator 24 is positioned so that magnetic lines of flux 26 will cross the ICPM 14. A cylindrically-shaped metallic slug 28 is positioned in the orifice 12 directly above the ICPM 14. The metallic slug 28 is dimensioned so that its upper surface 30 is either flush with or extends only slightly above the skull 13. In this figure, and in the subsequent figures, the ICPM and slug are shown loosely positioned in the orifice for clarity. However in actual usage, the orifice is dimensioned so that the ICPM and slug side surfaces make abutting contact with the surface defining the orifice. The skin 34 of the recipient is positioned over the slug 28. A perspective view of the slug 28 is shown in FIG. 3. As shown in FIG. 4, the metallic slug is coated with an epoxy layer 29 chosen to be inert with respect to flesh and bone. This coating covers the entire slug and is necessary to insure that metal contained within the slug 28 will not react with the recipient's body after implantation. However other inert coatings could be utilized such as, for example, glass. Additionally, a perspective view of the ICPM 14 is shown in FIG. 5, the top portion being partially cut away to show a magnetic pick-up coil 36 positioned therein.

In operation, the ICPM 14 is placed within the orifice 12 so that its pressure-sensitive surface 16 contacts the dura 20. A typical ICPM such as one described in U.S. patent application Ser. No. 012,142 is less than five millimeters thick. Skull thicknesses vary with the individual but may be as much as twenty millimeters thick. The cylindrically-shaped slug 28 can be chosen to have any height, the height being determined by the distance between the top surface of the ICPM 14 and the outer surface of the skull 13. If the magnetic field generator 24 is chosen to have a flux density sufficiently great to operate the ICPM 14 when the magnetic pick-up coil 36 is flush with the outer surface of the skull 13, then the flux density may not be sufficient to operate the ICPM 14 if the pick-up coil 36 is, for example, located fifteen millimeters below the skull 13 outer surface. However, by utilizing the metallic slug 28 as above described, flux density at the pick-up coil 36 can be made to be substantially the same as it would have been if the pick-up coil 36 were located flush with the outer surface of the skull 13. Thus the surgeon, upon locating the ICPM 14 within the orifice 12, would select from a kit of slugs the particular one having the necessary height, thereby allowing a magnetic field generator 24 having a constant and known output flux density to be utilized.

A further embodiment of the invention is shown in FIG. 6. Here, an orifice 40 is formed in a skull 42 so that its sides extend inwardly from the upper surface of the skull 42 at a predetermined angle until they intersect a cylindrically-shaped portion extending downwardly to the inner surface of the skull 42. The cylindrically-shaped portion is chosen so that it is substantially equal to the height of the ICPM 14. A magnetic field generator 44 is provided in accordance with the discussion above. The metallic slug 48 in this embodiment is in the form of a truncated cone as can be seen in perspective in FIG. 7. Although not shown, the slug 48 is also coated with an inert material as explained in conjunction with FIG. 4.

In a still further embodiment of the invention shown in FIG. 8, a metallic slug 52 is the shape of a truncated cone as shown in FIG. 6 is externally located with respect to the skin 54 of the recipient and held in place by a bandage 56. Although a bandage 56 is utilized in this particular embodiment, any other type of holding means could be utilized. A magnetic field generator 58 is located above the metallic slug 52 which concentrates magnetic lines of flux 60 from the generator 58 at the surface of the ICPM 62.

In the exemplary embodiment the slug is formed of a shaped piece of ferrous or ferrite material. The ferrite may be composed of an amalgam of both ferrous and non-ferrous metals which exhibit a property which allows the propagation of magnetic lines of flux through the material without dispersion. Examples of such materials are ferroxcube type 3C8 or 4C4 ferrite and ar well known in the magnetic arts.

It should now be apparent that a magnetic field concentrator for use in conjunction with a implanted device has been described wherein the concentrator can either be implanted or mounted externally to the implanted device. Magnetic lines of flux generated by a magnetic field generator are intercepted by the concentrator and provided to the implanted device, the magnetic flux lines thus provided having a higher density than would be present without the concentrator.

What is claimed is:

1. In a system including an implanted device having a magnetic field pick-up means for converting magnetic energy to electrical energy for energizing said implnated device, and an external magnetic field generator located so that magnetic lines of flux generated thereby intersect said pick-up means, a means for concentrating a portion of said magnetic lines of flux at said pick-up means comprising a metallic slug located between said generator and said pick-up means, thereby concentrating said magnetic lines of flux at said pick-up means.

2. The means for concentrating of claim 1 wherein said slug comprises a ferrite material.

3. The means for concentrating of claim 2 further comprising means for positioning said slug between said generator and said implanted device.

4. The means for concentrating of claim 2 wherein said slug is adapted to be implanted substantially adjacent to said implanted pick-up means, said means for concentrating further comprising a coating material encasing said slug, said coating being chosen to be substantially inert to a recipient's body.

5. The means for concentrating of claim 4 wherein said pick-up means comprises a magnetic pick-up coil and said slug is formed in the shape of a truncated cone and oriented so that a plane defined by the smaller of said cone end surfaces is adjacent to said substantially parallel to a plane defined by said magnetic pick-up coil.

6. The means for concentrating of claim 4 wherein said implnated device is an intracranial pressure monitoring device (ICPM) adapted so that at least a part thereof extends into an orifice formed in a recipient's skull, and said slug is adapted so that at least a part thereof also extends into said orifice.

7. The means for concentrating of claim 4 wherein said pick-up means comprises a magnetic pick-up coil and said slug is cylindrically-shaped and oriented so that a plane defined by one of said slug end surfaces is substantially parallel to a plane defined by said magnetic pick-up coil.

8. A medical system comprising:

an implanted device having an magnetic field pick-up means for converting magnetic energy to electrical energy for energizing said implanted device;

a magnetic field generator for generating magnetic lines of flux to be intercepted by said pick-up means; and a metallic slug located between said implanted device and said generator for increasing the density of said magnetic lines of flux at said magnetic pick-up means.

9. The system of claim 8 wherein said slug is in the shape of a cylinder.

10. The system of claim 8 wherein said slug is in the shape of a truncated cone.

11. The system of claim 8 further comprising means for positioning said slug between said generator and said implanted device.

12. A method for increasing the magnetic flux density at an implanted device having a magnetic pick-up means for converting magnetic energy to electrical energy for energizing said implanted device, the steps comprising:

locating a magnetic field generator a predetermined distance from said pick-up means; and placing a metallic slug between said generator and said pick-up means, thereby increasing the flux density at said pick-up means.

* * * * *